US010806764B2

(12) United States Patent
Kuo et al.

(10) Patent No.: US 10,806,764 B2
(45) Date of Patent: Oct. 20, 2020

(54) ANTI-AGING METHOD AND COMPOSITION

(71) Applicant: NuLiv Science USA, inc., Brea, CA (US)

(72) Inventors: Chia-Hua Kuo, Taipei (TW); Jinfu Wu, Taipei (TW); Michael Chang Yu Wang, Brea, CA (US)

(73) Assignee: NULIV SCIENCE USA, INC., Brea, CA (US)

( * ) Notice: Subject to any disclaimer, the term of this patent is extended or adjusted under 35 U.S.C. 154(b) by 0 days.

(21) Appl. No.: 15/989,704

(22) Filed: May 25, 2018

(65) Prior Publication Data

US 2019/0374592 A1    Dec. 12, 2019

(51) Int. Cl.
*A61K 36/00* (2006.01)
*A61K 36/258* (2006.01)
*A61K 36/738* (2006.01)

(52) U.S. Cl.
CPC .......... *A61K 36/258* (2013.01); *A61K 36/738* (2013.01)

(58) Field of Classification Search
None
See application file for complete search history.

(56) References Cited

U.S. PATENT DOCUMENTS

2015/0099032 A1* 4/2015 Roumayeh ............ A23L 33/105
426/2

OTHER PUBLICATIONS

European Search Report dated Sep. 25, 2019 in counterpart European application 19176647.6, 10 pages.
Min et al. article, "The change of effective compounds in Rosa roxburghii Tratt dry wine and Rosa roxburghii Tratt juice," Food and Fermentation Industries, Jan. 1, 2014, 4 pages in Chinese.
Kaneko et al., "Accelerated recovery from cyclophosphamide-induced leukopenia in mice administered a Japanese ethical herbal drug, Hochu-ekki-to," Medline, U.S. National Library of Medicine, Nov. 1, 1999, 2 pages.
Korivi et al., "Anti-oxidative effect of ginsenoside Rg1 against exhaustive exercise-induced proteins and lipids oxidation in liver of rats," 57th annual meeting of the American College Sports-Medicine Inaugural World Congress on Exercise 15, vol. 42, No. 5, suppl. 1, Apr. 30, 2010, 2 pages.

* cited by examiner

*Primary Examiner* — Qiuwen Mi
(74) *Attorney, Agent, or Firm* — Juan Carlos A. Marquez; Marquez IP Law Office, PLLC

(57) ABSTRACT

Disclosure of the invention is related to an herbal composition comprising (1) *Panax ginseng* extract or *Panax notoginseng* extract and (2) *Rosa roxburghii* extract, at an amount to activate phagocytic macrophage in association with the senescent cell clearance of a human subject who completes an acute route of aerobic exercise. Also provided is an anti-aging method which comprises administering a subject in need thereof the herbal composition.

10 Claims, 5 Drawing Sheets
Specification includes a Sequence Listing.

SEQUENCE LISTING

<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: 18S ribosomal forward primer

<400> SEQUENCE: 1
acaggattga cagattgata gctc                                    24

<210> SEQ ID NO 2
<211> LENGTH: 21

```
<212> TYPE: DNA
<213> ORGANISM: Artificial Sequence
<220> FEATURE:
<223> OTHER INFORMATION: 18S ribosomal reverser primer

<400> SEQUENCE: 2
tcgctccacc aactaagaac g                                           21

<210> SEQ ID NO 3
<211> LENGTH: 24
<212> TYPE: DNA
<213> ORGANISM: Artificial Sequence
<220> FEATURE:
<223> OTHER INFORMATION: 18S ribosomal Probe

<400> SEQUENCE: 3
tgcaccacca cccacggaat cgag                                        24

<210> SEQ ID NO 4
<211> LENGTH: 18
<212> TYPE: DNA
<213> ORGANISM: Artificial Sequence
<220> FEATURE:
<223> OTHER INFORMATION: IL-6 forward primer

<400> SEQUENCE: 4
cagtggacag gtttctga                                               18

<210> SEQ ID NO 5
<211> LENGTH: 18
<212> TYPE: DNA
<213> ORGANISM: Artificial Sequence
<220> FEATURE:
<223> OTHER INFORMATION: IL-6 reverse primer

<400> SEQUENCE: 5
ttcggcaaat gtagcatg                                               18

<210> SEQ ID NO 6
<211> LENGTH: 26
<212> TYPE: DNA
<213> ORGANISM: Artificial Sequence
<220> FEATURE:
<223> OTHER INFORMATION: IL-6 probe

<400> SEQUENCE: 6
ccattaacaa caacaatctg aggtgc                                      26

<210> SEQ ID NO 7
<211> LENGTH: 20
<212> TYPE: DNA
<213> ORGANISM: Artificial Sequence
<220> FEATURE:
<223> OTHER INFORMATION: iNOS forward primer

<400> SEQUENCE: 7
agcgggatga ctttccaaga                                             20

<210> SEQ ID NO 8
<211> LENGTH: 21
<212> TYPE: DNA
<213> ORGANISM: Artificial Sequence
<220> FEATURE:
<223> OTHER INFORMATION: iNOS reverse primer

<400> SEQUENCE: 8
```

```
taatggaccc caggcaagat t                                           21
```

<210> SEQ ID NO 9
<211> LENGTH: 30
<212> TYPE: DNA
<213> ORGANISM: Artificial Sequence
<220> FEATURE:
<223> OTHER INFORMATION: iNOS probe

<400> SEQUENCE: 9

```
cctgcaagtt aaaatccctt tggccttatg                                  30
```

ANTI-AGING METHOD AND COMPOSITION

FIELD OF THE INVENTION

The present invention relates to an anti-aging method through a supplement of a composition of (1) *Panax ginseng* extract or *Panax notoginseng* extract, and (2) *Rosa roxburghii* extract after an acute bout of aerobic exercise.

BACKGROUND OF THE INVENTION

Cells in human body are constantly aging, dying, and regenerating to evolve a multicellular system with a wide range of cell ages (Spalding et al., Retrospective birth dating of cells in humans. *Cell.* 2005; 122(1): 133-43). In skeletal muscle, cell lifespan varies greatly among different cell types. For example, myofibers are long-lived and endothelial cells in capillary age rapidly with a half-life ~2 weeks (Spalding et al., Retrospective birth dating of cells in humans. *Cell.* 2005; 122(1): 133-43; and Erben et al., Histological assessment of cellular half-life in tissues in vivo. *Histochem Cell Biol.* 2008;130(5):1041-6). Accumulation of senescent cells in tissues during aging implicated functional decay in animals and humans (Baker et al., Clearance of p16$^{Ink4a}$-positive senescent cells delays ageing-associated disorders. *Nature.* 2011; 479(7372):232-6), largely associated with inhibited cell renewing capacity (Kuilman et al., The essence of senescence. *Genes Dev.* 2010; 24(22):2463-79). The quantity of senescent cells could be reflected by senescence beta-galactosidase at pH 6.0 (Kurz et al., Senescence-associated (beta)-galactosidase reflects an increase in lysosomal mass during replicative ageing of human endothelial cells. *J Cell Sci.* 2000; 113(20): 3613-22). However, the SA-β-gal phenotype in normal human tissues was rarely reported.

Phagocytosis by macrophage is an innate mechanism to selectively eliminate senescent cells, which can occur in a rapid pace (Kay, Mechanism of removal of senescent cells by human macrophages in situ. *Proc Natl Acad Sci USA.* 1975; 72 (9): 3521-5). One way to attract macrophage into skeletal muscle is to perform a session of resistance exercise containing eccentric muscle contractions (Paulsen et al., Time course of leukocyte accumulation in human muscle after eccentric exercise. *Med Sci Sports Exerc.* 2010; 42(1): 75-85; and Malm et al., Immunological changes in human skeletal muscle and blood after eccentric exercise and multiple biopsies. *J Physiol.* 2000; 529(1): 243-62.). CD 68+ phagocytic macrophage infiltration into the challenged tissues is essential for recognition and elimination of damaged cells by phagocytosis (Ritschka et al., The senescence-associated secretory phenotype induces cellular plasticity and tissue regeneration. *Genes Dev.* 2017; 31(2): 172-83; and Tidball, Regulation of muscle growth and regeneration by the immune system. *Nat Rev Immunol.* 2017; 17(3):165-78). This process helps to establish an ideal microenvironment for tissue regeneration (Tidball & Wehling Henricks, Macrophages promote muscle membrane repair and muscle fibre growth and regeneration during modified muscle loading in mice in vivo. *J Physiol.* 2007; 578(Pt 1):327-36).

It is still desirable to develop an anti-aging method aiming to eliminate senescent cells in skeletal muscle.

SUMMARY OF THE INVENTION

Accordingly, the present invention provides an anti-aging method aiming to eliminate senescent cells in skeletal muscle using exercise after consumption of an herbal composition that potentially stimulates phagocytic function of macrophage for in situ senescent cell clearance.

In one aspect, the invention provides an herbal composition comprising (1) *Panax ginseng* extract or *Panax notoginseng* extract or a combination thereof, and (2) *Rosa roxburghii* extract, at an amount to activate phagocytic macrophage in association with the senescent cell clearance of a human subject who completes an exercise, wherein the herbal composition is standardized to contain 30% to 40% (weight % in total) of a total saponin, 0.6% to 2.0% of Vitamin C, and 2.0% to 4.0% of polyphenols, and a ginsenoside Rg1 (Rg1), as one indicator component ranging from 5 mg to 50 mg for one serving.

In another aspect, the invention provides an anti-aging method comprising administering to a human subject in need thereof an herbal composition to activate phagocytic macrophage in association with the senescent cell clearance of said human subject after his/her completing of an acute bout of aerobic exercise, wherein the herbal composition comprises (1) *Panax ginseng* extract or *Panax notoginseng* extract and (2) *Rosa roxburghii* extract, and is standardized to contain a total saponin of 30%-40%, Vitamin C of 0.6% to 2.0%, and polyphenols of 2.0%-4.0%, and Rg1 as one indicator component ranging from 5 mg to 50 mg for one serving.

In one example of the invention, the *Panax ginseng* extract is a water and/or ethanol extract of the roots of *Panax ginseng*.

In one example of the invention, the *Panax notoginseng* extract is a water and/or ethanol extract of the roots of *Panax notoginseng*.

In one example of the invention, the *Rosa roxburghii* extract is a water and/or ethanol extract of the fruits of *Rosa roxburghii*.

In one example of the invention, the herbal composition (also called as the P+R supplement herein) comprises (1) *Panax ginseng* extract or *Panax notoginseng* extract, and (2) *Rosa roxburghii* extract at a ratio of 4:1 ~1:4, for example 1:1.

In another example of the invention, the herbal composition consists essentially of (1) *Panax ginseng* extract or *Panax notoginseng* extract and (2) *Rosa roxburghii* extract at a ratio of 4:1~1:4, for example 1:1.

In one more example of the invention, the herbal composition consists of (1) *Panax ginseng* extract or *Panax notoginseng* extract and (2) *Rosa roxburghii* extract at a ratio of 4:1~1:4, for example 1:1.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment, which is presently preferred. It should be understood, however, that the invention is not limited to this embodiment.

The foregoing summary, as well as the following detailed description of the invention, will be better understood when read in conjunction with the appended drawings. For the purpose of illustrating the invention, there are shown in the drawings embodiment which is presently preferred. It should be understood, however, that the invention is not limited to this embodiment.

In the drawings:

Figure 1:
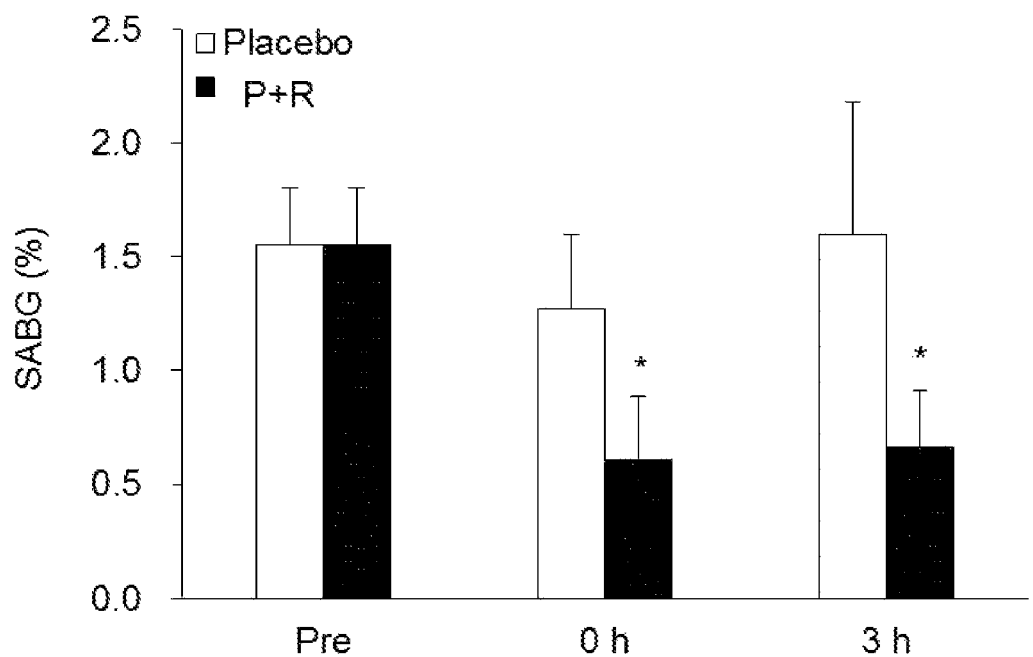

FIG. 1 provides the results of the senescence-associated β-galactosidase (SA-β-gal) in human muscle of the participants treated with the P+R supplement before and after an acute bout of aerobic exercise, showing that in the participants treated before the exercise with the P+R supplement (standardized to contain Rg1 at the amount of 5 mg), SA-β-gal in vastus lateralis muscle decreased after a 1-h cycling at 70% $\dot{V}O_{2max}$; wherein the values were presented as number of positive signal in 100 muscle fibers (%) (*: Significant difference from Pre, P<0.05; Abbreviation: Placebo, PLA).

Figure 2A:
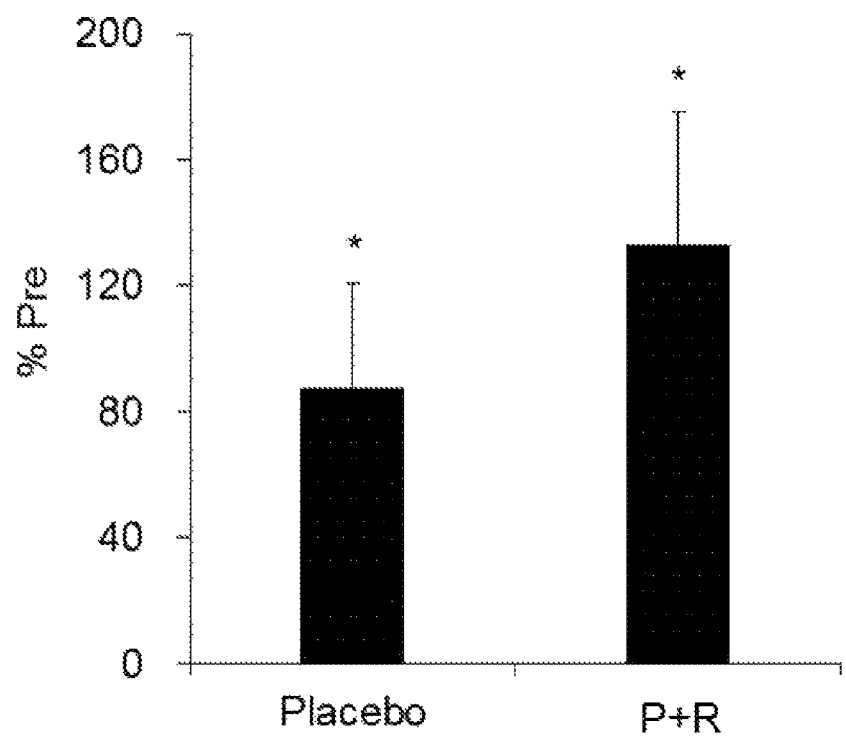
Figure 2B:
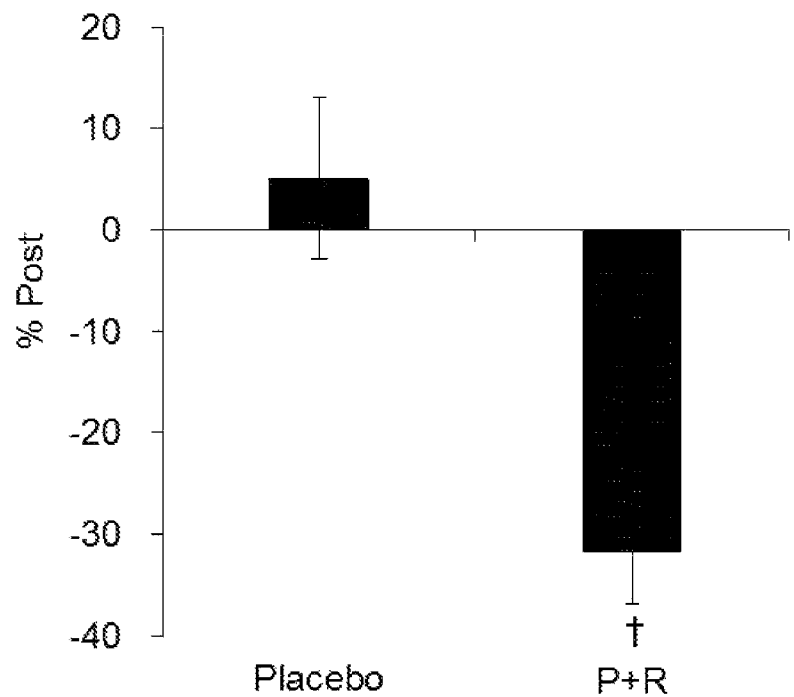

FIG. 2(A) provides the results of the apoptotic DNA nuclei in the human muscle before exercise (% Pre). FIG. 2(B) shows the results of apoptotic nuclei in vastus lateralis muscle in the participants treated with the P+R supplement 1 h after exercise (% Post) reverses during a 3-h recovery (wherein the values normalized to 0 h post-exercise); wherein the values were presented as number of positive signal in 100 muscle fibers (%) (*: significant difference from Pre, P<0.01; †:Significant difference from PLA, P<0.01; Abbreviation: Placebo, PLA).

Figure 3A:
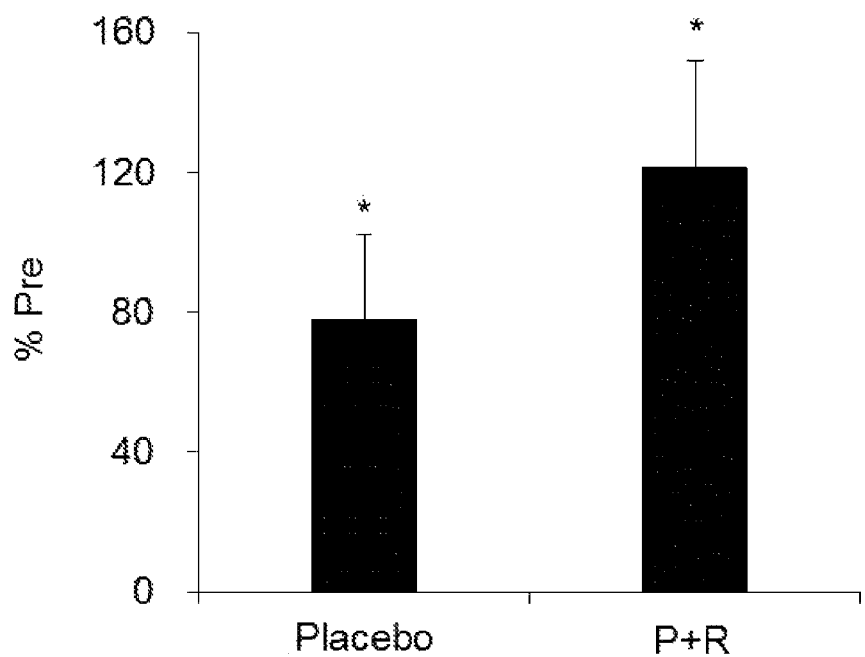
Figure 3B:
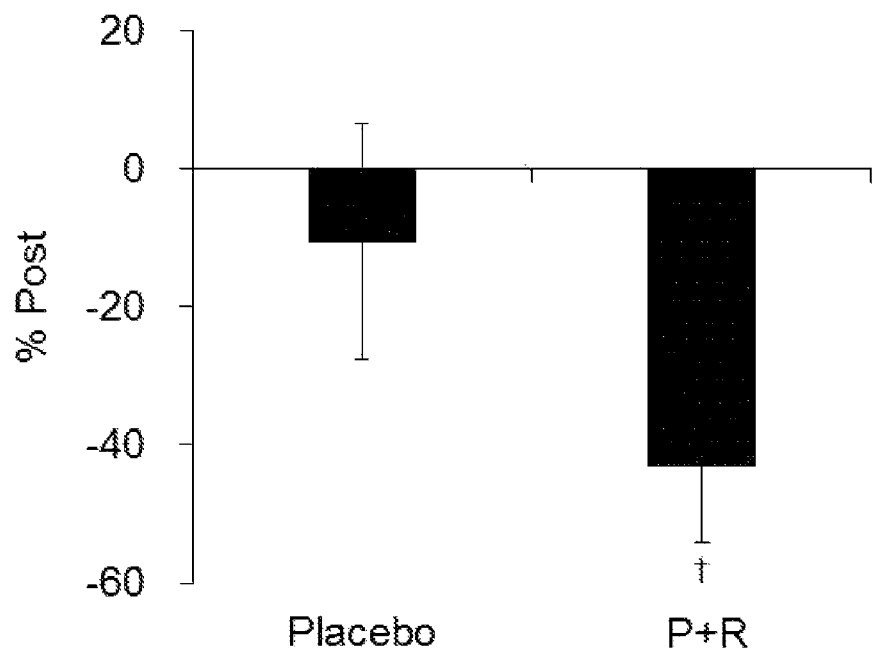

FIG. 3(A) shows that the leukocyte infiltration increased after exercise in both groups treated with PLA and the P+R supplement, wherein the values were normalized to Pre during a 3-h recovery. FIG. 3(B) shows the leukocyte infiltration reverses faster during a 3-h recovery in the group treated with the P+R supplement compared with the group treated with PLA. Values are presented as number of aggregates in 100 muscle fibers (%), and normalized to 0 h post-exercise (*: Significant difference from Pre, P<0.01; †:Significant difference from 0 h post-exercise, P<0.01; Abbreviation: Placebo, PLA).

Figure 4:
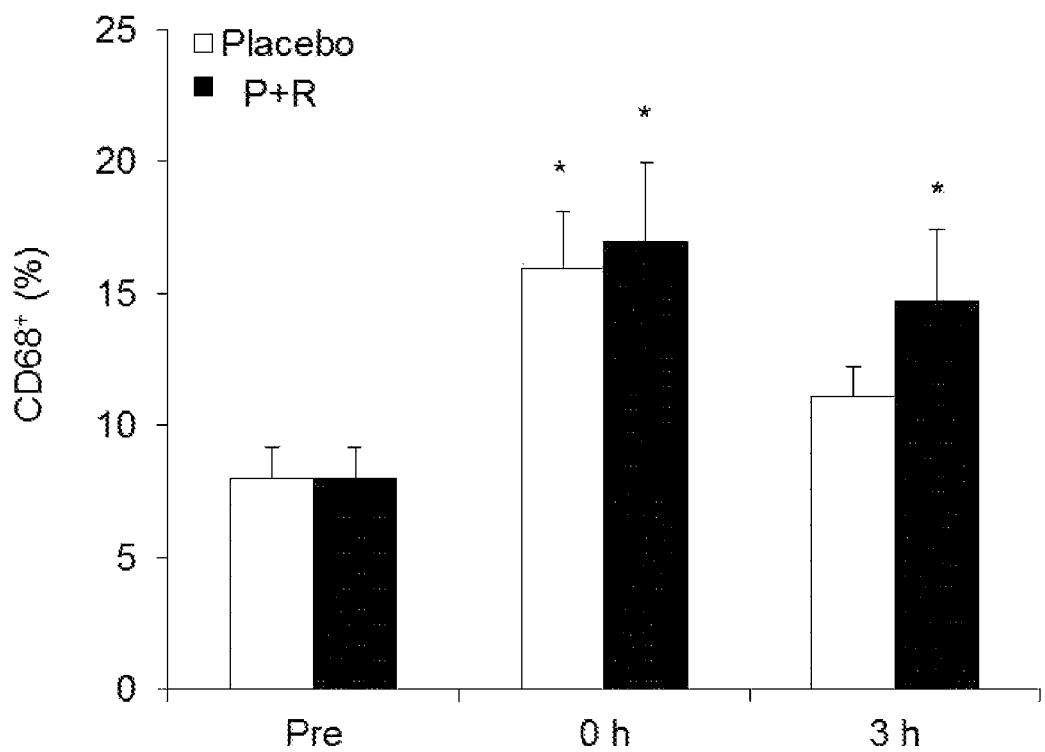

FIG. 4 provides the results of the CD 68$^+$ macrophage infiltration in human muscle after exercise, showing that the CD 68$^+$ macrophage increased after 1 h cycling at 70% $\dot{V}O_{2max}$ both in the groups treated with the P+R supplement and PLA; wherein the values were presented as number of CD 68$^+$ signal in 100 muscle fibers (%) (*: Significantly difference from Pre, P<0.05; Abbreviation: Placebo, PLA).

Figure 5A:
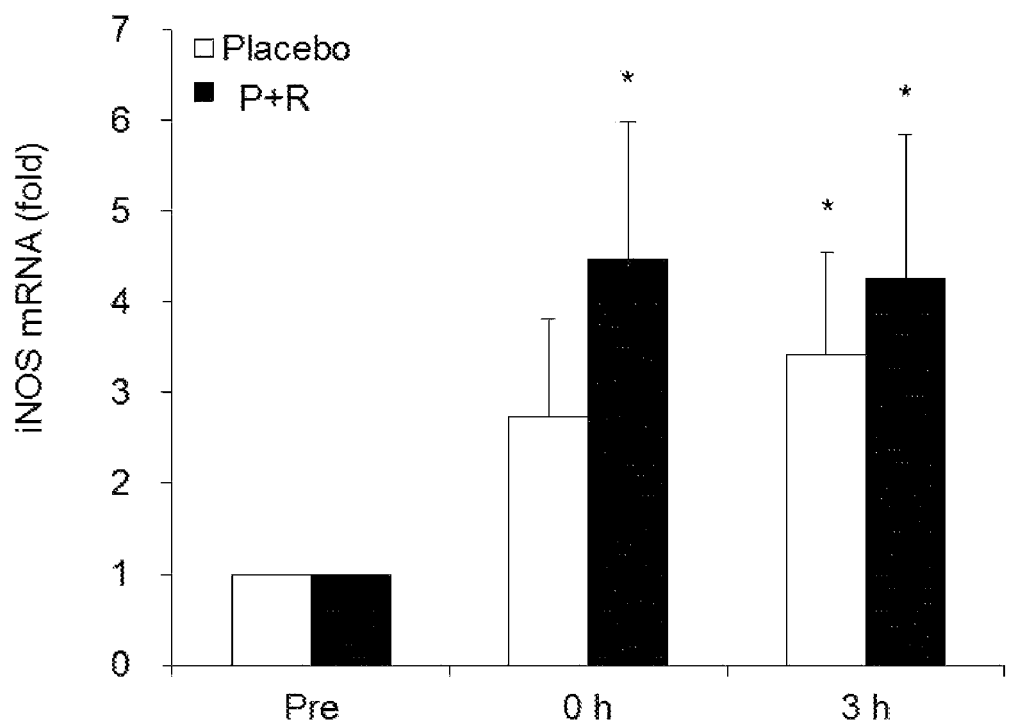

FIG. 5(A) provides the mRNA levels of inducible nitrate oxide synthase (iNOS) in human muscle after exercise, showing an earlier increase in vastus lateralis in the group treated with the P+R supplement.

Figure 5B:
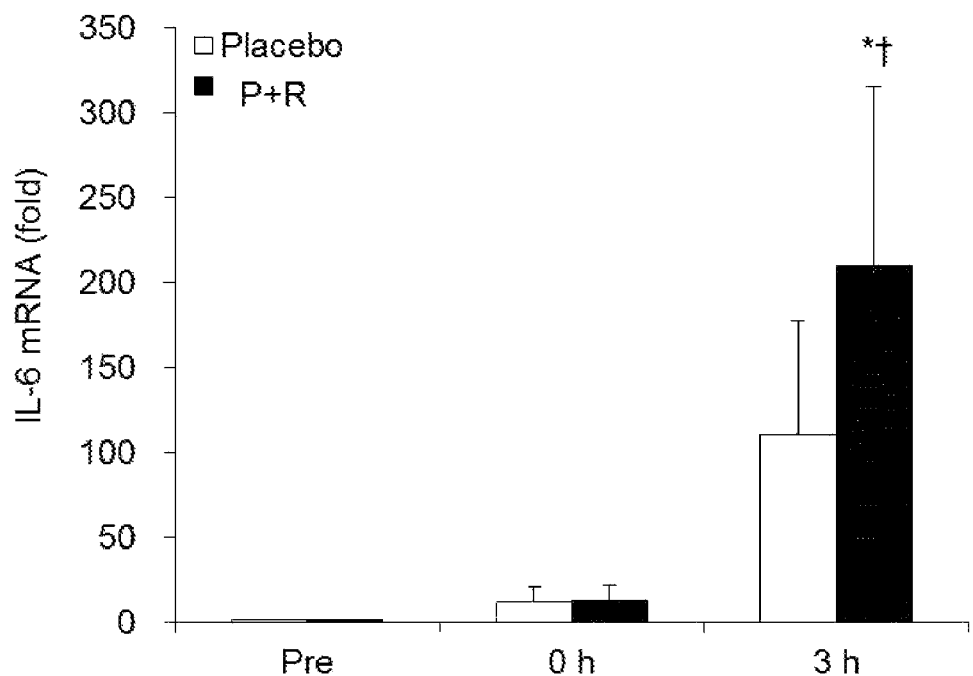

FIG. 5(B) provides the mRNA levels of interleukin 6 (IL-6) in human muscle after exercise in both the groups treated with PLA and the P+R supplement during a 3-h recovery, showing that the increase was further amplified, to a greater extent, for the group treated with the P+R supplement as compared with the group treated with PLA; wherein the values were normalized to 18S ribosomal RNA value.

Figure 5C:
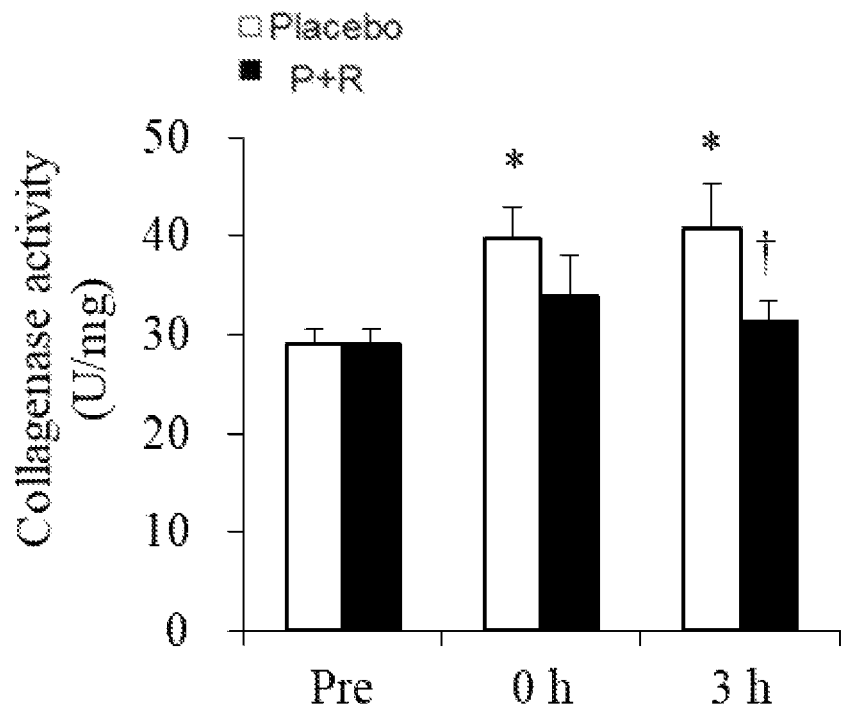

FIG. 5(C) provides the levels of the collagenase activity during the 3-h post-exercise, showing an increase after exercise only in the group treated with PLA; wherein the collagenase activity was lower in the group treated with the P+R supplement, as compared with the group treated with PLA; wherein the collagenase activity values were normalized to total collagen content (*: Significant difference from Pre, P<0.05; †:Significant difference from PLA, P<0.05; Abbreviation: Placebo, PLA).

Figure 6:
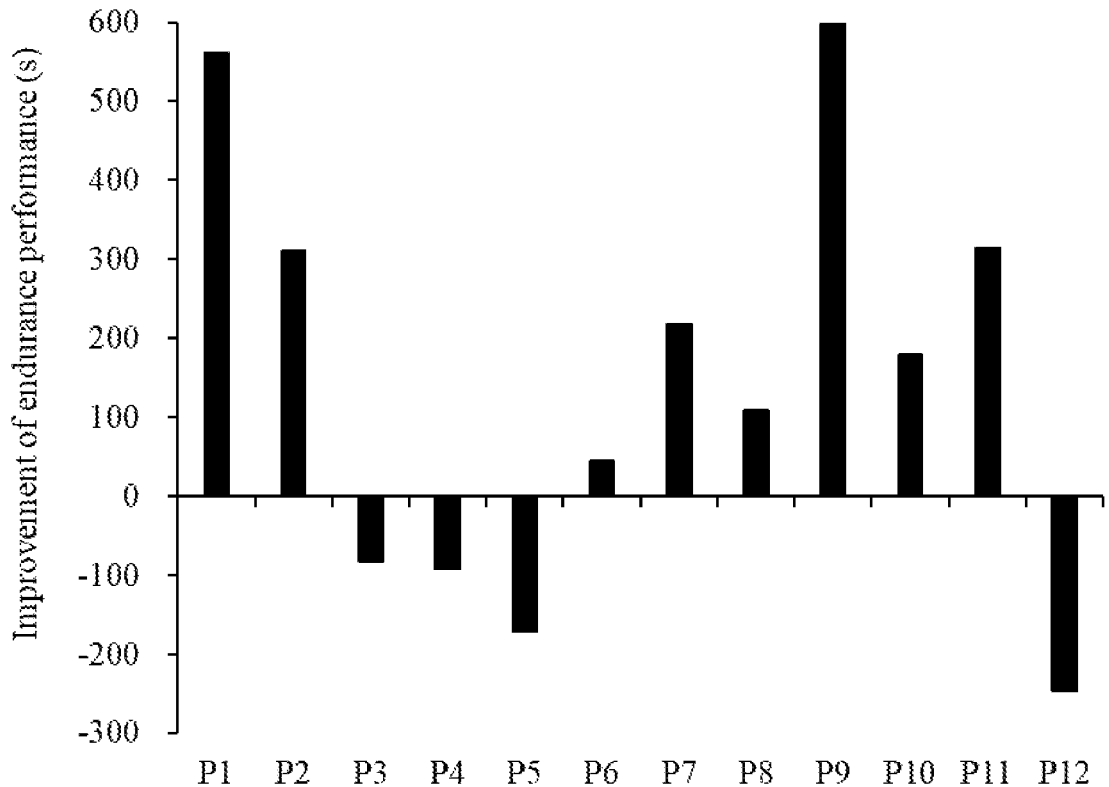

FIG. 6 shows that the cycling performance at 80% VO2max was improved by the P+R supplement; wherein the individual bar length was represented the riding time difference between the groups treated with PLA and P+R supplement of each participant (assessed by cycloergometer exercise at 80% $\dot{V}O2max$) (Abbreviation: Second, S; Placebo, PLA).

DETAILED DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

It is unexpectedly found in the present invention that the senescent cells of exercised human skeletal muscle can be decreased by the supplementation with an herbal composition of (1) *Panax ginseng* extract or *Panax notoginseng* extract or a combination thereof and (2) *Rosa roxburghii* extract. Accordingly, the present invention provides an herbal composition comprising, or consisting essentially of, or consisting of, (1) *Panax ginseng* extract or *Panax notoginseng* extract or a combination thereof and (2) *Rosa roxburghii* extract at an amount to activate phagocytic macrophage in association with the senescent cell clearance of a human subject who completes an exercise, wherein the herbal composition is standardized to contain 30%-40% of a total saponin, 0.6% to 2.0% of Vitamin C of, and 2.0%-4.0% of polyphenols, and Rg1 as one indicator component ranging from 5 mg to 50 mg for one serving.

On the other hand, the invention provides an anti-aging method, which comprises administering to a human subject in need thereof an herbal composition to activate phagocytic macrophage in association with the senescent cell clearance of said human subject after his/her completing of an acute bout of aerobic exercise, wherein the herbal composition comprises (1) *Panax ginseng* extract or *Panax notoginseng* extract and (2) *Rosa roxburghii* extract, and is standardized to contain 30% to 40% of a total saponin, 0.6% to 2.0% of Vitamin C, and 2.0% to 4.0% of polyphenols, and Rg1 as one indicator component ranging from 5 mg to 50 mg for one serving.

According to the invention, the herbals may be extracted with water, ethanol or a combination thereof, which may be obtained by any commonly used method or standard method. In the invention, either *Panax ginseng* or *Panax notoginseng* can be used to provide a ginsenoside Rg1 (Rg1) as one indicator component, which may be obtained from the extraction of the roots of *Panax ginseng* or *Panax notoginseng* with water or/and ethanol. In one example, the In one particular example, the extraction of *Panax ginseng* or *Panax notoginseng* comprises the steps of:

washing the raw materials;

pulverizing the materials through a size 20 mesh screen and repeating the extraction of the materials with water to obtain a water extract;

centrifuging and concentrating the water extract, and running it through an absorptive resin column; and collecting the eluent, further washing, and concentrating the extract as obtained prior to storage.

In the invention, the *Rosa roxburghii* extract may be obtained by the extraction with water and/or ethanol by any commonly used method or standard method. In one particular example, the *Rosa roxburghii* extract was obtained by the process of the steps of:

washing the fresh fruits of *Rosa roxburghii*, and repeating the extraction of the fruits with water at a low temperature in an anaerobic condition to obtain a crude extract;

filtering the crude extract and discarding the solid matter to obtain a filtrate;

evaporating the filtrate at a low temperature and in an anaerobic condition; and purifying, drying and grinding the paste to a specific mesh size to obtain the final extract.

In the invention, the herbal composition may be formulated using any standard technology or commonly used methods known to those skilled in the art. The herbal composition comprises the extract of *Panax ginseng* or *Panax notoginseng* and the extract of *Rosa roxburghii* extract, at a ratio of 4:1~1:4. In one particular example, the herbal composition consists of (or consists essentially of) the two extracts at a ratio of 1:1.

In the invention, the herbal composition, also called as "the P+R supplement" hereinafter, comprises, or consists essentially of, or consist of, (1) *Panax ginseng* extract or *Panax notoginseng* and (2) *Rosa roxburghii* extract, at a ratio of 4:1~1:4, for example 1:1, which is standardized to contain 30%-40% of total saponins, 0.6%-2.0% of Vitamin C, and 2.0%-4.0% of total polyphenols, and Rg1 as one indicator component ranging from 5 mg to 50 mg (e.g., 5 mg) for one serving. One example of the P+R supplement is the product with the brand name of ActiGin® supplied by Nuliv Science, USA.

The term "ginsenoside Rg1" or "Rg1" as used herein refers to a compound having the chemical name: (3β, 6α, 12β)-3,12-Dihydroxydammar-24-ene-6,20-diyl bis-β-D-glucopyranoside, which is a major component of the root and stem of ginseng plant.

The term "effective amount" as used herein refers to an amount of a drug or pharmaceutical agent which, as compared to a corresponding subject who has not received such amount, results in an effect in treatment or prevention of a disease, disorder, or side effect, or a decrease in the rate of advancement of a disease or disorder. The term also includes within its scope amounts effective to enhance normal physiological function.

The term "a physiologically acceptable carrier" as used herein refers to a carrier, diluent, or excipient that is physiologically acceptable, in the sense of being compatible with the other ingredients of the formulation and not deleterious to the subject to be administered with the composition. Any carrier, diluent or excipient commonly known or used in the field may be used in the invention, depending to the requirements of the formulation.

The present invention will now be described more specifically with reference to the following examples, which are provided for the purpose of demonstration rather than limitation.

EXAMPLES

Example 1

Preparation of the Herbal Composition According to the Invention

The herbal composition according to the invention may be obtained by combining the extract of *Panax ginseng* or *Panax notoginseng*, and *Rosa roxburghii* extract, wherein the herbals were extracted with water and/or ethanol.

To obtain the water extract of *Panax ginseng* roots, the raw materials was washed and pulverized through a size 20 mesh screen; the water extraction was then centrifuged, concentrated. The solution as obtained run through an absorptive resin column and the eluent was collected, further washed, and concentrated prior to storage.

The fruits of *Rosa roxburghii* were washed and repeatedly extracted with mater at low temperature in an anaerobic condition. Then, the solid matter was filtered and discarded to obtain a filtrate; and the filtrate was then subject to an evaporation at low temperature in an anaerobic condition to obtain a paste. The paste as obtained was purified, dried and ground to a specific mesh size to obtain the final extract.

The *Panax ginseng* extract and the *Rosa roxburghii* extract were mixed at the ratio of 4:1-1:4, and then standardized to contain 30%-40% of total saponins, 0.6%-2.0% of Vitamin C, and 2.0%-4.0% of total polyphenols, and Rg1 as one indicator component ranging from 5 mg to 50 mg (e.g., 5 mg) for one serving, which was called as "the P+R supplement" as used for the following human trials.

Example 2

Human Trials 2.1 Participants

The human trials were approved by Institutional Review Board of University of Taipei (IRB-2015-004) in accordance with the Declaration of Helsinki. All the participants gave their written informed consent after explanation about the experimental procedure and potential risks and benefits of participation.

In the study for determination of SA-β-gal, apoptotic DNA fragmentation, and macrophage infiltration of human skeletal muscle after high intensity cycling exercise under the treatment with the P+R supplement (also called as "the P+R supplementation"), there were twelve (12) volunteered participants who were recreationally active men (age 21±0.2 years, height 171±2.2 cm, body mass 65±3.7 kg; $\dot{V}O_{2max}$ 48±1.1 ml·kg$^{-1}$·min$^{-1}$).

In the study to confirm ergogenic effect of the P+R supplementation, there were twelve male participants (age 23±0.5 years, height 173±0.9 cm, body mass 66±2.0 kg; $\dot{V}O_{2max}$ 45±2.5 ml·kg$^{-1}$·min$^{-1}$).

Participants were familiarized with the experimental procedures used in each experiment, and then measured the $\dot{V}O_{2max}$ in incremental test on a cycloergometer (Monark 839E, Stockholm, Sweden) before the trial. Participants warmed up for 1 min with no load prior to the test, and then performed the incremental test starting at 100 W and increasing by 25 W every 3 min until exhaustion. Pulmonary gas exchange was measured during the test with a gas analysis system (Cortex Biophysik GmbH, Leipzig, SN, Germany). Participants maintained a cadence at 60 rpm during the test. The cessation of test was judged when pedaling frequency fell below 50 rpm for two times despite verbal encouragement, or a plateau in the oxygen uptake despite an increased power output and a respiratory exchange ratio above 1.1.

2.2 Experiment Procedures

Each of the trials was conducted in a randomized double blind placebo controlled crossover manner. Participants attended to the laboratory and were divided into two groups: one group treated with PLA and the other treated with the P+R supplement, for a washout period of at least four weeks between each trial. Participants were provided a standard isocaloric diet 12 h prior to each trial. Biopsied muscle samples were collected immediately and during 3 h recovery.

Participants received the P+R supplement or PLA 1 h before exercise on a cycloergometer (Monark 839E, Stockholm, Sweden). Participants exercised 1 h always on the same bike ergometer at the power output of 70% $\dot{V}O_{2max}$ with cadence 60 rpm. Participants consumed a high carbohydrate (GI: 80) meal (80% carbohydrate, 8% fat and 12% protein) containing 1.5 g carbohydrates per kg body weight. They were allowed to drink additional water ad libitum. The meal was consumed within 10 min after exercise.

To determine endurance performance, separate twelve participants received the P+R supplement or PLA I h before the test. Participants warmed up for 5 min at a work rate (watt) of 60% $\dot{V}O_{2max}$, and then pedaled on the same Monark cycle ergometer at 80% $\dot{V}O_{2max}$ until exhaustion with the same experimental design.

2.3 Muscle Biopsy

Muscle biopsies were taken from vastus lateralis muscle before (Pre), immediately (0 h) and 3 h after exercise, under local anesthesia (2% lidocaine) using a 18G Temno disposable cutting needle (Cardinal Health, Waukegan, Ill., USA) inserted into the vastus lateralis positioned at 3 cm depth, 20 cm proximal to knee cap. Baseline muscle biopsy in the vastus lateralis was conducted 4 weeks before exercise challenge in this trial. Two additional muscle biopsies were conducted again immediately after and 3 h after 1 h cycling at 70% $\dot{V}O_{2max}$ on contralateral leg at the same position. Muscle tissue was quickly removed from the needle, and disposed into a conical vial containing 10% formalin. Paraffin-embedded tissue was sectioned in paralleled with trials. Other biopsied samples were frozen directly in liquid nitrogen and stored for later biochemical determination of mRNA expression.

2.4 Phagocytic Macrophage and SA-β-gal Positive Cells

Immunofluorescence and hematoxylin and eosin (H&E) staining were used together to identify phagocytic macrophage (CD 68$^+$) infiltration. VECTASTAIN® Universal Quick Kit (PK 8800) (Vector Laboratories, Burlingame, Calif., USA) was used for CD 68$^+$ analysis. Immunohistochemistry was used to detect the SA-β-gal positive cells. Universal DAB Detection Kit (REF 760-500) (Ventana Medical Systems, Tucson, Ariz., USA) was used for SA-β-gal analysis at pH 6 according to the manufacturer's instruction. Primary antibodies used were rabbit anti-human CD 68$^+$ (1:200, ab955) (Abcam, Cambridge, Mass., USA) and mouse anti-human beta-galactosidase-1/GLB1 antibody (1:150, NBP2-45731) (Novus Biologicals Europe, Abingdon, OXF, UK). The slides were reviewed at a magnification of ×200 and ×400 by a certified pathologist. The cells positive markers were quantified and expressed as positive signal number/total skeletal muscle fiber number (%). A total of 600 muscle fibers were included for analysis. All data were repeated by a certified pathologist from the Taipei Institute of Pathology and a specialist at the University with similar results.

2.5 Apoptotic DNA Fragmentation

Apoptotic DNA fragmentation was identified by a fluorometric TUNEL detection kit (Mebstain Apoptosis Kit Direct, #8445) (Medical & Biological Laboratories, Woburn, Mass., USA) according to the manufacturer's instructions for both muscle cross-sections. Briefly, tissue sections were incubated with a fluorescein conjugated TUNEL reaction. Negative control experiments were performed by omitting the TdT enzyme in the TUNEL reaction mixture on the tissue sections. After TUNEL labeling, the muscle sections were mounted with 4',6-diamidino-2-phenylindole (DAPI, H-1200) (Vector Laboratories, Burlingame, Calif., USA). TUNEL and DAPI-positive nuclei staining were captured under a fluorescence microscope (Olympus BX51, Olympus Corporation, Tokyo, Japan). The number of TUNEL and DAPI-positive nuclei were counted from overall cross-section at 20× objective magnification. Only the TUNEL-positive nuclei overlapping fiber nuclei were quantified as apoptotic nuclei. The TUNEL labeling was quantified as the number of TUNEL-positive nuclei per 600 muscle fibers.

2.6 Leukocyte Infiltration

For histological analysis, H&E staining was used to identify leukocyte infiltration into muscle tissues on cross-sections. Leukocyte infiltration was judged by visible inflammatory cell invasion, hypercontraction, or coagulative cytoplasm. The percentage of leukocyte infiltration fibers were calculated from a total 600 fibers. The sections were observed under a light microscope (Olympus BX51, Olympus Corporation, TKY, Japan), and digital images were taken covering the entire cross section of the vastus lateralis.

2.7 RNA Analysis

Frozen muscle samples (about 15 mg) were homogenized, and total RNA was extracted using the TM Reagent (T9424-200) (Sigma, St. Louis, Mo., USA), followed by precipitation with isopropanol, two ethanol washes, drying, and suspension in 20 μl nuclease-free water. The total RNA was quantified and verified spectrophotometrically at absorbance of 260/280 nm (Thermo Fisher Scientific, Madison, Wis., USA). One microgram of RNA in a total volume of 20 μl was used to reverse transcribe by using iScript cDNA Synthesis Kit (#170-8890) (Bio-Rad, Hercules, Calif., USA) according to manufacturer's instruction and then stored at −20° C. for subsequent quantitative PCR analysis.

Real-time PCR was performed using MyiQ Single Color Real-Time PCR Detection System (Bio-Rad, Hercules, Calif., USA), TaqMan Probe (Sigma-Aldrich, Singapore) and iQ Supermix kit (#170-8860) (Bio-Rad, Hercules, Calif., USA). A relative RT-PCR method using 18S ribosomal RNA as an internal standard was used to determine relative expression levels of the target mRNAs. The primers and probe used to amplify target mRNA are 18S ribosomal (18S): Forward (5'-3'): ACAGGATTGACAGATTGA-TAGCTC (SEQ ID NO: 1), Reverse (5'-3'): TCGCTCCAC-CAACTAAGAACG (SEQ ID NO: 2), Probe (5'-3'): TGCACCACCACCCACGGAATCGAG (SEQ ID NO: 3); interleukin 6 (IL-6) : Forward (5'-3'): CAGTGGACAG-GTTTCTGA (SEQ ID NO: 4), Reverse (5'-3'): TTCG-GCAAATGTAGCATG (SEQ ID NO: 5), Probe (5'-3'): CCATTAACAACAACAATCTGAGGTGC (SEQ ID NO: 6); and inducible nitric oxide synthase (iNOS): Forward (5'-3'): AGCGGGATGACTTTCCAAGA (SEQ ID NO: 7), Reverse (5'-3'): TAATGGACCCCAGGCAAGATT (SEQ ID NO: 8), Probe (5'-3'): CCTGCAAGTTAAAATC-CCTTTGGCCTTATG (SEQ ID NO: 9). Series of baseline of cDNA samples were diluted in five successive fivefold or twofold to estimate the PCR efficiencies (>90%) by interpolating the slope of standard curve relating the Ct value. For each PCR reaction, 18S gene was co-amplified with each target cDNA. To control for any variations due to efficiencies of the reverse transcription and PCR, the results were expressed as a ratio of target mRNA/18S.

2.8 Total Collagenase Activity

Collagenase (a family of matrix metalloproteinase or MMPs) activity colorimetric assay kit (K792-100) (BioVision, Milpitas, Calif., USA) was used to determine collagenase activity according to the manufacturer's protocol. Homogenized sample (10 μl) was added in 96-well plate for assay. The absorbance was measured kinetically at 345 nm in a microplate reader at 37° C. for 30 min.

2.9 Data Analyses

All data were expressed as means±SE. The data were analyzed using a two-factor repeated-measures ANOVA (SPSS 20.0). Post hoc analysis was performed using Paired Student's t test. The level of significance was set at P<0.05.

2.10 Results

2.10.1 Senescence Associated Beta-Galactosidase (SA-β-gal)

Based on physician tracking and participant self-reports, none of them reported any adverse events due to the P+R supplementation or muscle biopsy throughout the studies.

Immunohistochemical staining analysis indicated existence of SA-β-gal positive signal in less than 2% of myofibers from vastus lateralis at baseline (Pre) (see FIG. 1). No detectable change in SA-β-gal of muscle were observed after a 1-h cycling exercise at 70% $\dot{V}O_{2max}$ during the PLA trial. In a contrary, significantly declines in SA-β-gal (from 1.6% to ~0.6%, P<0.05) were observed after the same exercise when the P+R supplement was orally supplemented 1 h before an acute bout of aerobic exercise (Pre vs. 0 h, P<0.05; Pre vs. 3 h, P<0.05).

2.10.2 Apoptotic DNA Fragmentation

Apoptotic DNA fragmentation in the muscles after the 1-h exercise was identified by TUNEL staining, expressed as the number of positive signals in a hundred muscle fibers (%). There are ~6% positive signals for apoptotic DNA fragmentation detected in the biopsied muscle at Pre. Apoptotic DNA fragmentation of the muscle increased significantly after exercise in both of the groups treated with PLA and the P+R supplementation, respectively (main effect of exercise, P<0.01). In the group treated with the P+R supplement, a greater exercise-induced increase in apoptotic DNA fragmentation was found (PLA: +87% vs. P+R: +133%, P<0.05), see FIG. 2(A). During the 3-h post-exercise recovery, the positive signals for apoptotic DNA fragmentation reversed significantly (from 12.8 to 8.5%, P<0.01) only in the group treated with the P+R supplement, but not in the group treated with PLA, see FIG. 2(B).

2.10.3 Leukocyte Infiltration

The leukocyte infiltration in the muscles were detected, expressed as the number of the cell infiltration sites in a hundred muscle fibers (%). There were ~2% of human skeletal muscle showing leukocyte infiltration prior to the exercise (Pre). After exercise, leukocyte infiltration in vastus lateralis increased in the two groups treated with PLA and the P+R supplementation (main effect of exercise, P<0.01). A greater exercise-induced increase was found in leukocyte infiltration (PLA: +78% vs. P+R: +121%, P<0.05), see FIG. 3(A). During the 3-h post-exercise recovery, a trend of earlier reversal of leukocyte infiltration in skeletal muscle was observed during the P+R supplementation, compared with the PLA trial (PLA: −11% vs. P+R: −43%, P=0.06), see FIG. 3(B).

2.10.4 CD 68$^+$ Macrophage Infiltration

The CD 68$^+$ macrophage in the muscles was identified by immunofluorescence staining. For both the groups treated with PLA and the P+R supplementation, the levels of CD 68$^+$ macrophage in the muscles increased significantly after exercise (+2 folds, P<0.05) than those before the exercise (Pre). During the 3-h recovery, this increase was reversed without significant group difference, see FIG. 4.

2.10.5 Inflammatory Markers

To determine macrophage activation, iNOS mRNA (FIG. 5(A)) and IL-6 mRNA (FIG. 5(B)) responses against exercise were also measured. An earlier increase in iNOS mRNA of the muscle was observed during the P+R supplementation as compared with the PLA supplementation (PLA: +2.7 folds vs. P+R: +4.5 folds, group effect: P<0.05). It was found that the P+R supplementation also enhanced the exercise-induced IL-6 response (PLA: 110 folds vs. P+R: 209 folds, P<0.05). Total collagenase (MMPs) activity of the muscles was measured, as compared with those prior to exercise (Pre), see FIG. 5(C). After an acute route of aerobic exercise, collagenase activity of the muscle increased transiently (+38%, P<0.05) in the group treated with PLA, but not in the group treated with the P+R supplement.

2.10.6 Cycling Performance at 80% $\dot{V}O_{2max}$ Improved by the P+R Supplementation Endurance performance was assessed by cycloergometer exercise at 80% $\dot{V}O_{2max}$. The P+R supplementation significantly increased cycling time to exhaustion by 12% (PLA: 1219±135 s vs. P+R: 1364±145 s, P<0.05) and power output by 13% (PLA: 199±31 kJ vs. P+R: 225±33 kJ, P<0.05). Eight of twelve participants treated with the P+R supplement showed a significant improvement in cycling time as compared with the group treated with PLA, see FIG. 6.

It can be concluded in that high intensity cycling transiently increased apoptosis together with leukocyte and macrophage infiltrations into challenged skeletal muscle; however, this condition was not sufficient to influence senescent cell number in skeletal muscle. Further, it was suggested that macrophage activation by the P+R supplementation was associated with the senescent cell clearance of exercised human skeletal muscle.

The disclosure will become more fully understood from the said embodiment for illustration only and thus does not limit the disclosure. Any modifications within the spirit and category of the disclosure fall in the scope of the disclosure.

We claim:

1. An anti-aging method comprising administering to a human subject in need thereof an herbal composition at an amount effective to activate phagocytic macrophage in association with the senescent cell clearance of said human subject after his/her completing of an acute bout of aerobic exercise, wherein the herbal composition comprises (1) *Panax ginseng* extract or *Panax notoginseng* extract and (2) *Rosa roxburghii* extract, and is standardized to contain 30% to 40% of a total saponin, 0.6% to 2.0% of Vitamin C, and 2.0% to 4.0% of polyphenols, and ginsenoside Rg1 (Rg1) as one indicator component ranging from 5 mg to 50 mg for one serving.

2. The method according to claim 1, wherein the herbal composition comprises (1) *Panax ginseng* extract or *Panax notoginseng* extract and (2) *Rosa roxburghii* extract at a ratio of 4:1~1:4.

3. The method according to claim 2, wherein the ratio is 1:1.

4. The method according to claim 1, wherein the herbal composition consists essentially of (1) *Panax ginseng* extract or *Panax notoginseng* extract and (2) *Rosa roxburghii* extract at a ratio of 4:1~1:4.

5. The method according to claim 4, wherein the ratio is 1:1.

6. The method according to claim 1, wherein the herbal composition consists of (1) *Panax ginseng* extract or Panax notoginseng extract and (2) *Rosa roxburghii* extract at a ratio of 4:1~1:4.

7. The method according to claim 6, wherein the ratio is 1:1.

8. The method according to claim 1, wherein the *Panax ginseng* extract is a water extract of the roots of *Panax ginseng*.

9. The method according to claim 1, wherein the *Panax notoginseng* extract is a water extract of the roots of *Panax notoginseng*.

10. The method according to claim 1, wherein the *Rosa roxburghii* extract is a water extract of the fruits of *Rosa roxburghii*.

* * * * *

UNITED STATES PATENT AND TRADEMARK OFFICE
CERTIFICATE OF CORRECTION

PATENT NO. : 10,806,764 B2
APPLICATION NO. : 15/989704
DATED : October 20, 2020
INVENTOR(S) : Chia-Hua Kuo et al.

It is certified that error appears in the above-identified patent and that said Letters Patent is hereby corrected as shown below:

On the Title Page

In the Abstract, in Line 6:
Please delete the word "route" and insert the word --bout--

In the Specification

In Column 10, under 2.10.5 Inflammatory Markers, Line 24:
Please delete the word "route" and insert the word --bout--

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*